US00PP19760P2

(12) United States Plant Patent
Meilland

(10) Patent No.: US PP19,760 P2
(45) Date of Patent: Feb. 24, 2009

(54) SHRUB ROSE PLANT NAMED 'MEIKLUTZ'

(50) Latin Name: *Rosa hybrida*
Varietal Denomination: Meiklutz

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 11/980,489

(22) Filed: Oct. 31, 2007

(51) Int. Cl.
*A01H 5/00* (2006.01)

(52) U.S. Cl. ..... Plt./107
(58) Field of Classification Search ..... Plt./107
See application file for complete search history.

(56) References Cited

U.S. PATENT DOCUMENTS

PP7,282 P * 7/1990 Noack ..... Plt./101

* cited by examiner

*Primary Examiner*—Wendy C. Haas
(74) *Attorney, Agent, or Firm*—Buchanan Ingersoll & Rooney PC

(57) ABSTRACT

A new and distinct variety of Shrub Rose plant is provided that abundantly forms attractive small cup-shaped pink blossoms. A bushy and compact growth habit is displayed and the foliage is rather dense and semi-glossy. The disease tolerance is good particularly with respect to *Marsonina rosea.* The plant is well suited for providing attractive ornamentation in the landscape, such as in parks and gardens.

1 Drawing Sheet

Figures 1, 2, 3, 4, 5, 6, 7, 8, 9, 10, 11, 12, 13, 14, 15, 16, 17:
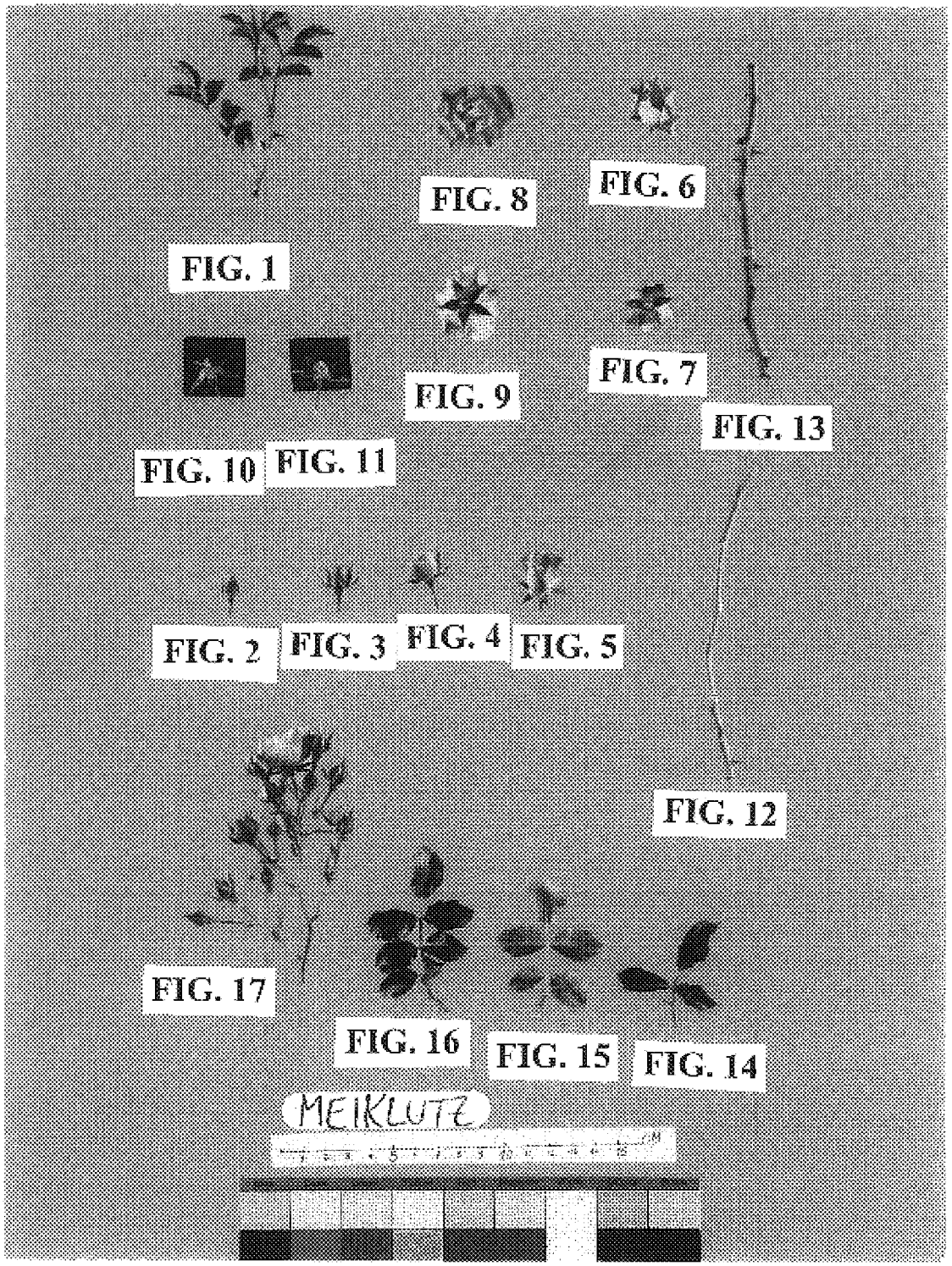

Botanical/commercial classification: *Rosa hybrida*/Shrub Rose Plant.
Varietal denomination: cv. Meiklutz.

SUMMARY OF THE INVENTION

The new variety of *Rosa hybrida* shrub rose plant was created by artificial pollination wherein two parents were crossed which previously had been studied in the hope that they would contribute the desired characteristics. The female parent (i.e., the seed parent) was the product of the cross of the 'Noatraum' variety (U.S. Plant Pat. No. 7,282) and an unnamed seedling (non-patented in the United States). The 'Noatraum' variety is marketed under the FLOWER CARPET Pink Trademark. The male parent (i.e., the pollen parent) was 'The Fairy' variety (non-patented in the United States).

('Noatraum'×Unnamed Seedling)×'The Fairy'.

The seeds resulting from the above pollination were sown and small plants were obtained which were physically and biologically different from each other. Selective study resulted in the identification of a single plant of the new variety.

It was found that the new Shrub rose plant of the present invention:

(a) exhibits a bushy and compact growth habit, (b) forms in abundance attractive small cup-shaped pink blossoms, (c) displays rather dense semi-glossy green foliage, (d) exhibits excellent tolerance to diseases particularly with respect to *Marsonina rosea,* and (e) is particularly well suited for growing as attractive ornamentation in the landscape.

The new variety well meets the needs of the horticultural industry and can be grown to advantage as attractive ornamentation in parks and gardens.

The new variety can be readily distinguished from its ancestors. For instance, the blossom appearance is considerably different from that of the 'Noatraum' and 'The Fairy' varieties. More specifically, the 'Noatraum' blossoms are larger and are darker pink in coloration. The blossoms of 'The Fairy' variety are lighter pink in coloration.

The new variety has been found to undergo asexual propagation in France by a number of routes, including budding, grafting, and the use of cuttings. Asexual propagation by the above-mentioned techniques in France has shown that the characteristics of the new variety are stable and are strictly transmissible by such asexual propagation from one generation to another.

The new variety has been named 'Meiklutz'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately one year of age and were observed during June while growing on *Rosa froebelli* understock outdoors at Le Cannet des Maures, Var, France. Dimensions in centimeters and a standard color presentation are indicated at the bottom of the photograph.

FIG. 1 — illustrates a specimen of a young shoot;

FIG. 2 — illustrates a specimen of a floral bud before the opening of the sepals;

FIG. 3 — illustrates a specimen of a floral bud at the opening of the sepals;

FIG. 4 — illustrates a specimen of a floral bud at the opening of the petals;

FIG. 5 — illustrates a specimen of a flower in the course of opening;

FIG. 6 — illustrates a specimen of an open flower — plan view — obverse;

FIG. 7 — illustrates a specimen of an open flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates a specimen of a leaf with three leaflets — plan view — upper surface;

FIG. 15 — illustrates a specimen of a leaf with five leaflets — plan view — under surface;

FIG. 16 — illustrates a specimen of a leaf with seven leaflets — plan view — upper surface; and FIG. 17 — illustrates a cluster of buds in various stages of opening together with an open flower.

DETAILED DESCRIPTION

The chart used in the identification of the colors is that of The Royal Horticultural Society (R.H.S. Colour Chart). The description is based on the observation of one-year-old plants during May while budded on *Rosa froebelli* understock and growing in greenhouses at Le Cannet des Maures, Var, France.

Class: Landscape Shrub Rose.

Plant:

*Habit.*—Bushy.

Branches:

*Color.*—Young stems: near Yellow-Green Group 144B. Adult wood: near Green Group 143A.

*Thorns.*—On young stems: Small prickles: Quantity: none. Long prickles: Configuration: upright and longish pointed, and slightly concave on the under surface with a narrow and long base. Quantity: approximately 7 on average on a stem length of 10 cm. Length: approximately 0.7 cm on average. Color near Greyed-Orange Group 164A. On adult stems: Small prickles: Quantity: none Long prickles: Configuration: upright and longish pointed, and slightly concave on the under surface with a narrow and long base. Quantity: approximately 8 on average on a stem length of 10 cm. Length: approximately 0.8 cm on average. Color near Greyed-Orange Group 177A.

Leaves:

*Stipules.*—Smooth, adnate, pectinate, rather broad, approximately 1.4 cm in length on average, approximately 0.6 cm in width on average, near Green Group 141B on the upper surface, and near Green Group 143B on the under surface.

*Petioles.*—Upper surface: near Yellow-Green Group 144A in coloration. Under surface: near Green Group 143B in coloration. Texture: smooth, non-glandular and without prickles on the upper and under surfaces. Length: approximately 1.7 cm for the terminal leaflet.

*Rachis.*—Upper surface: near Green Group 139C in coloration. Under surface: near Green Group 143B in coloration. Texture: smooth.

*Leaflets.*—Number 3, and most often 5 and 7. Shape: generally oval with a somewhat rounded tip and a rounded base. Size: the terminal leaflets commonly are approximately 3.9 cm in length. Serration: small and single (as illustrated). Texture: somewhat flexible. General appearance: rather dense with a semi-glossy aspect. Color (young foliage): upper surface: near Green Group 141A. Under surface: near Yellow-Green Group 146C. Color (adult foliage): Upper surface: near Green Group 139A. Under surface: near Yellow-Green Group 146B.

Inflorescence:

*Number of flowers.*—Commonly pluriflorous, with a plurality of blossoms per stem.

*Peduncle.*—Tomentose, approximately 1.5 cm in length on average, approximately 0.2 cm in diameter on average, and near Greyed-Purple Group 183A in coloration.

*Sepals.*—Upper surface: smooth and near Green Group 138B. Under surface: smooth and near Green Group 141B in coloration. Shape: longish and narrow, and tend to be upright at the base. Size: near 1.4 cm in length on average, and near 0.3 cm in width at the widest point on average.

*Buds.*—Shape: elongated. Size: small. Length: approximately 1.4 cm on average. Width: near 1 cm on average at the widest point. Color as the calyx breaks. Upper surface: near Red Group 55A, and suffused with Red Group 55B. Under surface: near Red Group 56A, and amply suffused with near Red Group 55A and 55B.

*Flower.*—Shape: cup-shaped. Diameter approximately 2.2 cm on average. Color (in the course of opening): Upper surface: near Red-Purple Group 62A, and amply suffused with near Red Group 55A. Under surface: near Red-Purple Group 62D, and suffused with near Red-Purple Group 62B. Spot at base: very small and near Green-White Group 157D on the upper surface and near White Group 155D on the under surface. Color (when fully open): Upper surface: near Red-Purple Group 62A suffused with near Red-Purple Group 57C. Under surface: near Red-Purple Group 56D suffused with near Red Group 55C, and amply suffused with near Red Group 55B. Spot at base: very small and near Green-White Group 157D on the upper surface and near White Group 155D on the under surface. Fragrance: none. Petal number: commonly approximately 10 to 16 on average under normal growing conditions. Petal shape: with a substantially rounded tip and base. Petal texture: relatively thick. Petal length: approximately 1.7 cm on average. Petal width: approximately 1.6 cm on average. Petal arrangement: imbricated; and commonly with petaloids towards the center. Petal drop: good with the petals commonly detaching cleanly before drying. Stamen number approximately 93 on average. Anthers: regularly arranged around the styles, approximately 0.1 cm in size on average, and near Yellow-Orange Group 23B in coloration. Pollen: present. Filaments: approximately 0.3 cm in length on average and near Yellow Group 2C in coloration. Pistils: approximately 30 on average. Stigmas: approximately 0.1 cm in Size on average and near Yellow Group 2C in coloration. Styles: approximately 0.4 cm in length on average, and near Green-Yellow Group 1C in coloration. Receptacle: tomentose, approximately 0.5 cm in length on average, approximately 0.4 cm in width on average at the widest point, and near Greyed-Purple Group 183B in coloration.

Development:

*Vegetation.*—Strong.

*Blooming.*—Late, very abundant, and recurrent.

*Tolerance to diseases.*—Very good, particularly with respect to *Marsonina rosae.*

I claim:

1. A new and distinct Shrub rose plant characterized by the following characteristics:

(a) exhibits a bushy and compact growth habit, (b) forms in abundance attractive small cup-shaped pink blossoms, (c) displays rather dense semi-glossy green foliage, (d) exhibits excellent tolerance to diseases particularly with respect to *Marsonina rosea,* and (e) is particularly well suited for growing as attractive ornamentation in the landscape;

substantially as herein shown and described.

* * * * *

MEIKLUTZ